US012650422B2

(12) United States Patent (10) Patent No.: US 12,650,422 B2
Brouwer et al. (45) Date of Patent: Jun. 9, 2026

(54) UTILITY OF PROTEIN IN THE PREDICTION OF IN VIVO EFFECTS

(71) Applicant: Qualyst Transporter Solutions, LLC, Durham, NC (US)

(72) Inventors: Kenneth R. Brouwer, Chapel Hill, NC (US); Christopher Black, Cary, NC (US); Jonathan Jackson, Raleigh, NC (US)

(73) Assignee: Qualyst Transporter Solutions, LLC, Durham, NC (US)

( * ) Notice: Subject to any disclaimer, the term of this patent is extended or adjusted under 35 U.S.C. 154(b) by 0 days.

(21) Appl. No.: 15/320,710

(22) PCT Filed: Oct. 7, 2015

(86) PCT No.: PCT/US2015/054411
§ 371 (c)(1),
(2) Date: Dec. 20, 2016

(87) PCT Pub. No.: WO2016/057626
PCT Pub. Date: Apr. 14, 2016

(65) Prior Publication Data
US 2017/0205393 A1 Jul. 20, 2017

Related U.S. Application Data

(60) Provisional application No. 62/060,916, filed on Oct. 7, 2014.

(51) Int. Cl.
*G01N 33/50* (2006.01)
*C12Q 1/26* (2006.01)

(52) U.S. Cl.
CPC ........... *G01N 33/5008* (2013.01); *C12Q 1/26* (2013.01); *G01N 33/5067* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 4,110,077 A | 8/1978 | Klein et al. |
| 6,780,580 B2 | 8/2004 | LeCluyse et al. |
| 7,601,494 B2 | 10/2009 | Tian et al. |
| 7,604,934 B2 | 10/2009 | LeCluyse et al. |
| 7,682,781 B2 | 3/2010 | LeCluyse et al. |
| 8,367,630 B2 | 2/2013 | Tian et al. |
| 8,658,353 B2 | 2/2014 | Fang et al. |
| 2003/0049840 A1 | 3/2003 | Demetriou et al. |
| 2004/0214226 A1 | 10/2004 | LeCluyse et al. |
| 2005/0048464 A1 | 3/2005 | Xianbin et al. |
| 2008/0262444 A1 | 10/2008 | Takada |
| 2010/0035293 A1 | 2/2010 | Brouwer et al. |
| 2010/0179798 A1 | 7/2010 | Subramanian et al. |

| | | | |
|---|---|---|---|
| 2013/0115271 A1 | 5/2013 | Zamboni et al. |
| 2016/0061820 A1 | 3/2016 | Novik et al. |
| 2019/0257817 A1 | 8/2019 | Brouwer et al. |

FOREIGN PATENT DOCUMENTS

| | | |
|---|---|---|
| AU | 2021269341 A1 | 12/2021 |
| AU | 2017329025 B2 | 1/2024 |
| CA | 3036704 A | 3/2018 |
| CA | 2962491 C | 3/2023 |
| CN | 1439049 A | 8/2003 |
| CN | 101822659 A | 9/2010 |
| CN | 104388536 A | 3/2014 |
| CN | 104694456 A | 6/2015 |
| CN | 107003299 A | 8/2017 |
| CN | 109964129 B | 4/2023 |
| EP | 2762573 A1 | 8/2014 |
| EP | 3204767 A1 | 8/2017 |
| EP | 3513194 A1 | 7/2019 |
| EP | 4109102 A1 | 12/2022 |
| EP | 4509835 A2 | 2/2025 |

(Continued)

OTHER PUBLICATIONS

Yang et al. "Culture conditions and types of growth media for mammalian cells." Biomedical Tissue Culture. InTech, 2012. (Year: 2012).*
HiMedia Laboratories, "Hank's Balanced Salt Solution 1X", HiMedia Cell Culture Production Information, available from the company's webpage, revision Jan. 2011 (Year: 2011).*
Brouwer et al. "In vitro methods to support transporter evaluation in drug discovery and development." Clinical Pharmacology & Therapeutics 94.1 (2013): 95-112. (Year: 2013).*
Office Action and Search Report corresponding to Chinese Patent Application No. 2015800655330 dated May 9, 2018.
Office Action corresponding to Israeli Patent Application No. 251605 dated Feb. 25, 2018.

(Continued)

*Primary Examiner* — Emily A Cordas
(74) *Attorney, Agent, or Firm* — Jenkins, Taylor & Hunt, P.A.

(57) ABSTRACT

A method of evaluating disposition and/or effect of a candidate compound in an in vitro culture and/or suspension to predict in vivo disposition and/or effect of the candidate compound, which can include the steps of providing a cell culture and/or suspension; exposing a candidate compound to the culture and/or suspension; exposing the culture and/or suspension to a media providing an in vivo relevant extracellular environment, such as a media comprising a component (such as a protein and/or other component, such as lipoproteins, bile acids, and endogenous compounds such as bilirubin) at a physiologic concentration or a concentration having characteristics, such as binding characteristics, similar to the physiological concentration; wherein any combination of any of the exposing steps can occur in any order or simultaneously; and evaluating in vitro disposition and/or effect of the compound to predict in vivo disposition and/or effect of the candidate compound.

16 Claims, No Drawings

(56)            References Cited

FOREIGN PATENT DOCUMENTS

| HK | 40009989 B | 10/2023 | | |
|----|------------|---------|---|---|
| IL | 251605 B | 1/2022 | | |
| JP | 2008-503204 | 2/2008 | | |
| JP | 2013017411 A | 1/2013 | | |
| JP | 5846570 B2 | 1/2016 | | |
| JP | 2009-138010 | 6/2019 | | |
| JP | 2020182475 A | 11/2020 | | |
| JP | 7090072 B2 | 6/2022 | | |
| JP | 7097697 B2 | 7/2022 | | |
| JP | 2022126725 A | 8/2022 | | |
| JP | 2023098948 A | 7/2023 | | |
| WO | WO 00/55355 A2 | 9/2000 | | |
| WO | WO 2005/118787 A2 | 12/2005 | | |
| WO | WO2012/119012 A1 | 9/2012 | | |
| WO | WO-2013063588 A1 * | 5/2013 | .......... | C12N 5/0062 |
| WO | WO2016/057626 A1 | 4/2016 | | |
| WO | WO2018053406 | 3/2018 | | |

OTHER PUBLICATIONS

Supplementary European Search Report corresponding to European Patent Application EP15848390 dated Jan. 22, 2018.

Gibaldi & Perrier (1982) Pharmacokinetics, 2nd Ed. By Milo Gibaldi and Donald Perrier. Marcel Dekker, 270 Madison Avenue, New York, NY 11016:12-14.

Griffith & Naughton (2002) Tissue engineering—current challenges and expanding opportunities. Science 295:1009-1014.

Hamadeh et. al. (2010) Application of Genomics for Identification of Systemic Toxicity Triggers Associated With VEGF-R Inhibitors. Chem Res Toxicol 23(6):1025-1033.

Marion et al. (2007) Use of sandwich-cultured hepatocytes to evaluate impaired bile acid transport as a mechanism of drug-induced hepatotoxicity. Mol Pharmaceutics 4(6):911-918.

Angelin et al. (1982) Hepatic uptake of bile acids in man. Fasting and postprandial concentrations of individual bile acids in portal venous and systemic blood serum. J Clin Invest 70:724-731.

Ansede et al. (2010) An in Vitro Assay to Assess Transporter-Based Cholestatic Hepatotoxicity Using Sandwich-Cultured Rat Hepatocytes. Drug Metab Dispos 38(2):276-280.

Chandra et al. (2001) Optimization of Culture Conditions for Determining Hepatobiliary Disposition of Taurocholate in Sandwich-Cultured Rat Hepatocytes. Vitro Cellular & Developmental Biology-Animal 37(6):380-385.

Chiang (2009) Bile acids: regulation of synthesis. J Lipid Res 50:1955-1966.

Dawson et al. (2012) In Vitro Inhibition of the Bile Salt Export Pump Correlates with Risk of Cholestatic Drug-Induced Liver Injury in Humans. Drug Metab and Dispos 40(1):130-138.

Hartman et al. (2010) Evaluation of the endothelin receptor antagonists ambrisentan, darusentan, bosentan, and sitaxsentan as substrates and inhibitors of hepatobiliary transporters in sandwich-cultured human hepatocytes. Can J Physiol Pharmacol 88:682-691.

International Search Report corresponding to International Application No. PCT/US2015/054411 dated Dec. 31, 2015.

Jackson et al. (2009) In vitro assessment of P450 induction potential of novel chemopreventive agents SR13668, 9-cis-UAB30, and pentamethychromanol in primary cultures of human hepatocytes. Chemica-Biological Interactions 179:263-272.

Kaimal et al. (2009) Differential Modulation of Farnesoid X Receptor Signaling Pathway by the Thiazolidinediones. KJ Pharmacol Exp Ther 330(1):125-134.

Kilford et al. (2008) Hepatocellular Binding of Drugs: Correction for Unbound Fraction in Hepatocyte Incubations Using Microsomal Binding or Drug Lipophilicity Data. Drug Metab Dispos 36(7):1194-1197.

Liu et al. (1999a) Correlation of Biliary Excretion in Sandwich-Cultured Rat Hepatocytes and in Vivo in Rats. Drug Metabolism and Disposition 27(6):637-644.

Liu et al. (1999b) Biliary excretion in primary rat hepatocytes cultured in a collagen-sandwich configuration. The American Physiological Society: G12-G14.

Liu et al. (1999c) Use of Ca2+ Modulation to Evaluate Biliary Excretion in Sandwich-Cultured Rat Hepatocytes. J of Pharm & Experimental Therapeutics 289(3):1592-1599.

Liu et al. (1998) Partial Maintenance of Taurocholate Uptake by Adult Rat Hepatocytes Cultured in a Collagen Sandwich Configuration. Pharmaceutical Research 15(10):1533-1539.

Magnasco et al. (2008) Cyclosporin and Organ Specific Toxicity: Clinical Aspects, Pharmacogenetics and Perspectives. Curr Clin Pharmacol 3(3):166-173.

Marion et al. (2012) Endogenous Bile Acid Disposition in Rat and Human Sandwich-Cultured Hepatocytes. Toxicol Appl Pharmacal 261:1-27.

Notification Concerning Transmittal of International Preliminary Report on Patentability corresponding to International Application No. PCT/US2015/054411 dated Apr. 11, 2017.

Ogimura et al. (2011) Bile salt export pump inhibitors are associated with bile acid-dependent drug-induced toxicity in sandwich-cultured hepatocytes. Biochemical and Biophysical Research Communications 416:313-317.

Pfeifer et al. (2013) Determination of Intracellular Unbound Concentrations and Subcellular Localization of Drugs in Rat Sandwich-Cultured Hepatocytes Compared with Liver Tissue. Drug Metab Dispos 41:1949-1956.

Poulin et al. (2012) Comparative Assessment of In Vitro-In Vivo Extrapolation Methods used for Predicting Hepatic Metabolic Clearance of Drugs. J Pharm Sci 101:4308-4326.

Swift et al. (2010) Sandwich-cultured hepatocytes: an in vitro model to evaluate hepatobiliary transporter-based drug interactions and hepatotoxicity. Drug Metabolism Reviews 42(3):1-26.

Turncliff et al. (2006) Effect of culture conditions on the expression and function of Bsep, Mrp2, and Mdr1a/b in sandwich-cultured rat hepatocytes. Biochemical Pharmacology 71:1520-1529.

Weiqiang et al. (2015) FXR antagonism of NSAIDs contributes to drug-induced liver injury identified by systems pharmacology approach. Scientific Reports 5:8114.

Yu et al. (2014) Identification of Trisubstituted-pyrazol Carboxamide Analogs as Novel and Potent Antagonists of Farnesoid X Receptor. Bioorg Med Chem 22(11): 2919-2938.

K. K. Wolf et al: "Effect of Albumin on the Biliary Clearance of Compounds in SandwichCultured Rat Hepatocytes", Drug Metabolism and Disposition, vol. 36, No. 10, Jul. 10, 2008 (Jul. 7, 2008), pp. 2086-2092.

Office Action corresponding to Chinese Patent Application No. 2015800655330 dated Jan. 25, 2019.

Office Action corresponding to European Patent Application No. 15848390.9 dated Jan. 21, 2019.

Office Action corresponding to Chinese Patent Application No. 2015800655330 dated Aug. 8, 2019. (Translation).

Notice of Publication corresponding to U.S. Appl. No. 16/333,804 dated Aug. 22, 2019.

Office Action (Examination Report) corresponding to Israeli Patent Application No. 251605 dated Jul. 25, 2019. (Translation).

Office Action (Notice of Reason for Rejection) corresponding to Japanese Patent Application No. 2017-538914 dated Oct. 30, 2019.

Office Action (Examiner's Report) corresponding to Canadian Patent Application No. 2,962,491 dated Nov. 22, 2019.

Notice of Publication corresponding to European Patent Application No. 17851704.1 dated Jun. 26, 2019.

Wong et al., "Evaluation of Serum as Incubation Medium for Biliary Clearance Prediction in Sandwich-Cultured Rat Hepatocytes," Drug Metabolism Reviews, vol. 44, Supp. 1 p. 44; Abstract No. p. 17 (2012).

Office Action corresponding to European Patent Application No. 15848390.9 dated Dec. 19, 2019.

Office Action (Decision of Rejection) corresponding to Japanese Patent Application No. 2017-538914 dated Mar. 9, 2020.

Examination report corresponding to Australian Patent Application No. 2015328138 dated Nov. 23, 2020.

Examiner's Report corresponding to Canadian Patent Application No. 2,962,491 dated Feb. 8, 2021.

(56)　　　　References Cited

OTHER PUBLICATIONS

Office Action corresponding to Israeli Patent Application No. 251605 dated Oct. 13, 2020. (Translation).
Office Action (Restriction Requirement) corresponding to U.S. Appl. No. 16/333,804 dated Oct. 30, 2020.
Office Action corresponding to Chinese Patent Application No. 2015800655330 dated Dec. 18, 2020.
Office Action corresponding to Indian Patent Application No. 201727011198 dated Dec. 22, 2020. (Translation).
Office Action corresponding to European Patent Application No. 17851704.1 dated Feb. 4, 2021.
Boyer et al., "Unpregulation of a basolateral FXR-dependent bile acid efflux transporter OSTa-OSTB in cholestasis in humans and rodents," Am. J. Physiol. Gastrointest. Liver Physiol. 290, G1124-G1130 (2006).
European Search Report corresponding to European Patent application No. 17851704 dated Feb. 21, 2020.
Jackson et al., "Cholestatic Drug Induced Liver Injury: A Function of Bile Salt Export Pump Inhibition and Farnesoid X Receptor Antagonism," Applied in Vitro Toxicology, vol. 4, No. 3 pp. 265-279 (2018).
Marion et al., "Differential Disposition of Chenodeoxycholic Acid versus Taurocholic Acid in Response to Acute Troglitazone Exposure in Rat Hepatocytes," Toxicological Sciences, vol. 120, No. 2, pp. 371-380 (Abstract) (2011).
Office Action corresponding to Indian Patent Application No. 201927012270 dated Jul. 29, 2021.
Office Action (Notice of Reason for Rejection) corresponding to Japanese Patent Application No. 2019-51230 dated Aug. 16, 2021.
Office Action corresponding to U.S. Appl. No. 16/333,804 dated May 12, 2021.
Yang et al., "Species Differences in Hepatobiliary Disposition of Taurocholic Acid in Human and Rat Sandwich-Cultured Hepatocytes: Implications for Drug-Induced Liver Injury," Journal of Pharmacology and Experimental Therapeutics, vol. 353, No. 2 pp. 415-423 (2015).
Communication under Rule 71(3) EPC, Intention to Grant, corresponding to European Patent Application No. 17851704.1 dated Dec. 17, 2021.
Office Action, Final Notice of Reason for Rejection, corresponding to Japanese Application No. 2017-538914 dated Oct. 28, 2021.
Decision of Rejection corresponding to Chinese Patent Application No. 2015800655330 dated Jul. 28, 2021.
Office Action, Notice of Reason for Rejection, corresponding to Japanese Patent Application No. 2020-118197 dated Jul. 14, 2021.
Hearing Notice corresponding to Indian Patent Application No. 201727011198 dated Aug. 25, 2021.
Notice of Allowance corresponding to Israeli Patent Application No. 251605 dated Aug. 23, 2021.
Letter reporting Notice of Allowance corresponding to Israeli Patent Application No. 251605 dated Sep. 22, 2021.
Office Action corresponding to Canadian Patent Application No. 2,962,491 dated Oct. 19, 2021.
Certificate of Patent corresponding to EP Application No. 17851704.1, Patent No. 3513184 dated Jun. 1, 2022.
Certificate of Patent corresponding to IL Application No. 251605. Patent No. 251605 dated Apr. 2, 2022.
Certificate of Patent corresponding to JP Application No. 2017538914, Patent No. 7087097 dated Jun. 30, 2022.
Certificate of Patent corresponding to JP Application No. 2019515230, Patent No. 7000072 dated Jun. 15, 2022.
Communication 69 EPC corresponding to EU Application No. 22184808.8 dated Jan. 9, 2023.
Decision of Rejection corresponding to Japanese Patent application No. 2020-118197 dated Dec. 4, 2022.
Decision to Grant corresponding to EP Patent Application No. 17851704.1 dated May 6, 2022.
Decision to Grant corresponding to Japan Patent Application No. 2019-515230.

Decision to Grant Corresponding to Japanese Patent application 2020-009635 dated May 30, 2022.
Examination Report No. 1 for corresponding AU Application No. 2017329025 dated Jan. 4, 2023.
Hallifax, David et al., "Evaluation of Hepatic Clearance Prediction Using in Vitro Data Emphasis on Fraction Unbound in Plasma and Drug Ionisation Using a Database of 107 Drugs", Journal of Pharmaceutical Science, vol. 101(8), Aug. 1, 2012, pp. 2645-2652.
Issues Patent Certificate corresponding to Canadian Patent application No. 2,962,491 dated Mar. 21, 2023.
Notice of Allowance corresponding to Canada Patent Application No. 2,002,401 dated Sep. 15, 2021.
Office Action (Decision of Rejection) corresponding to Japanese Patent Application No. 2020-118197 dated Dec. 5, 2022 English translation.
Office Action and Search Report corresponding to Chinese patent Application No. 2017800710341 dated Mar. 2, 2022.
Office Action corresponding to U.S. Appl. No. 16/333,804 Feb. 25, 2022.
Office Action corresponding to European Application No. 15 848 390.9 dated Mar. 25, 2022.
Office Action corresponding to Japanese Patent application No. 2020-118197 dated Jul. 19, 2021.
Office Action corresponding to Japanese Patent No. 2017-538914 dated Nov. 1, 2021.
Office Action Corresponding with Japanese Patent Application No. 2020-118197 dated Apr. 4, 2022.
Office Action Notice of Reason for Rejection corresponding to Japan Patent Application No. 2020-118187 dated Mar. 31, 2022.
Office Action Notice of Reason for Rejection, corresponding to Japanese Application No. 2017-538914 dated Jun. 9, 2021.
Order No. 62/2021 corresponding to Indian Patent Application No. 201727011198 dated Mar. 30, 2022.
Search Report corresponding to EU Application No. 22184808.8 dated Nov. 11, 2022.
Sigma-Aldrich, Dulbecco's Modified Eagle's Medium (DME), May 2007, Available online at: www.sigamaaldrich.com/deepweb/assets/sigmaaldrich/product/documents/261/153/d365pis.pdf (DMEM contains a predetermined glucose concentration, including 4.5 g/L).
Tetsuka et al., Species differences in sinusoidal and canalicular efflux transport of mycophenolic acid 7-0-glucuronide in sandwich-cultured hepatocytes, Pharmacology Research & Perspectives, vol. 2, e00035 (2014).
Oorts, et al., "Drug-induced cholestasis risk assessment in sandwich-cultured human hepatocytes." Toxicology in Vitro, vol. 34, 2016, 40 pages.
Susukida, et al., "Establishment of a Drug-Induced, Bile Acid-Dependent Hepatotoxicity Model Using HepaRG Cells," Journal of Pharmaceutical Sciences, vol. 105, No. 4, 2016, pp. 1550-1560.
Xiao, Y., et al., "Glucocorticoid treatment alters systemic bile acid homeostasis by regulating the biosynthesis and transport of bile salts," Digestive and Liver Disease, vol. 48, No. 7, 2016, pp. 771-779.
Yang, K., et al., "Sandwich-Cultured Hepatocytes as a Tool to Study Drug Disposition and Drug-Induced Liver Injury," Journal of Pharmaceutical Sciences, vol. 105, No. 2, 2016. pp. 443-459.
"Guideline on the Investigation of Drug Interactions", European Medicines Agency, Science Medicines Health, Committee for Human Medicinal Products (CHMP), Jun. 21, 2012, pp. 60.
"In Vitro Drug Interaction Studies—Cytochrome P450 Enzyme-and Transporter-Mediated Drug Interactions Guidance for Industry", U.S. Department of Health and Human Services Food and Drug Administration Center for Drug Evaluation and Research (CDER), Clinical Pharmacology Jan. 2020, pp. 46.
Baik, J., et al., "Transporter-Induced Protein Binding Shift (TIPBS): Hypothesis and Modeling", Optivia Biotechnology Inc., Oct. 18-22, 2015, p. 1.
Lefebvre, P., et al., "Role of Bile Acids and Bile Acid Receptors in Metabolic Regulation", Physiological Reviews, vol. 89, Issue 1, Jan. 2009, p. 147-191.
Sager, J.E., et al., "Physiologically Based Pharmacokinetic (PBPK) Modeling and Simulation Approaches: A Systematic Review of

(56)     References Cited

OTHER PUBLICATIONS

Published Models, Applications, and Model Verification", Minireview, Drug Metab Dispos, vol. 43, Nov. 2015, pp. 1823-1837.

Soroka, C.J., et al., "Mouse organic solute transporter alpha deficiency enhances renal excretion of bile acids and attenuates cholestasis", Hepatology, vol. 51, Issue 1, Jan. 2010, pp. 181-190.

Woodhead, J.L, et al., "Mechanistic Modeling Reveals the Critical Knowledge Gaps in Bile Acid-Mediated DILI", CPT Pharmacometrics Systems Pharmacology, vol. 3, No. 7, Jul. 2014, pp. 1-8.

Zhang, X., et al., "In Vitro Evidence of OATP1B1 Induced Drug-Serum Protein Binding Shift and Its Implications on Predicting Drug Clearance and Drug-Drug Interactions", Optivia Biotechnology, Oct. 27-28, 2016, p. 1.

Zhuang, X., et al., "PBPK modeling and simulation in drug research and development", Acta Pharmaceutica Sinica B, vol. 6, No. 5, 2016, pp. 430-440.

International Search Report and Written Opinion received in PCT Application No. PCT/US2017/052022, mailed Dec. 5, 2017, 15 pages.

International Preliminary Report on Patentability received in PCT Application No. PCT/US2017/052022, mailed on Mar. 28, 2019, 13 pages.

Extended European Search Report received in European Patent Application No. 17851704.1, mailed on Mar. 19, 2020, 6 pages.

Office Action received in Chinese Patent Application No. 201580065533.0 mailed on May 6, 2020, 16 pages. (Translation).

Office Action received in JP Patent Application No. 2019-515230 mailed on Aug. 23, 2021, 35 pages. (Translation).

Office Action received in CN Patent Application No. 201780071034.1 mailed on Dec. 31, 2021, 27 pages. (Translation).

Notification of Grant received in CN Patent Application No. 201780071034.1 mailed on Jan. 11, 2023, 4 pages. (Translation).

Notice of Allowance received in Canadian Patent Application No. 2,962,491 mailed on Jan. 16, 2023, p. 1.

Office Action (Notice of Reasons for Rejection) corresponding to Japanese Patent Application No. 2022-095609 dated Aug. 1, 2023, 47 pages. (Translation).

Office Action corresponding to U.S. Appl. No. 16/333,804 dated Aug. 2, 2023, 8 pages.

Office Action received in Canadian Patent Application No. 3036704 mailed on Nov. 23, 2023, 8 pages.

Notice of Acceptance received in Australian Patent Application No. 2017329025 mailed on Jan. 4, 2024, 4 pages.

Notice of Allowance corresponding to Israeli Patent Application No. 265390 dated Jan. 11, 2024, 7 pages. (Translation).

Intimation of Grant received in Indian Patent Application No. 201927012270 mailed on Jan. 15, 2024, 1 page.

Office Action received in EP Patent Application No. 22184808.8 mailed on Feb. 7, 2024. 5 pages.

De Bruyn, T., et al., "Sandwich-cultured hepatocytes: utility for in vitro exploration of hepatobiliary drug disposition and drug-induced hepatotoxicity", in Expert Opinion. Drug Metabolism & Toxicology, vol. 9. No. 5, 2013, pp. 589-616.

Examination Report received in Australian Patent Application No. 2021269341, mailed on May 31, 2024, 5 Pages.

Examination Report received in Australian Patent Application No. 2021269341, mailed on Jun. 26, 2024, 4 Pages.

Examiner's Report corresponding to Canadian Patent Application No. 3,036,704 dated Oct. 4, 2024, 3 Pages.

Final Office Action for U.S. Appl. No. 16/333,804, mailed on Jun. 10, 2024, 9 Pages.

Notice of Allowance corresponding to Canada Patent Application No. 2,962,491 dated Sep. 15, 2022.

Notice of Reasons for Refusal for Japanese Application No. JP2023061679, dated Jun. 18, 2024, 19 Pages.

Notice of Reasons for Refusal for Japanese Application No. 2023-061679, dated Jun. 25, 2024, 18 Pages.

Office Action (Decision to Grant) corresponding to Japanese Application No. 2017-538914 dated May 30, 2022.

Office Action (Notice of Reasons for Refusal) corresponding to Japanese Patent Application No. 2020-118197 dated Oct. 29, 2024, 32 pages. (Translation).

Office Action (Decision of Rejection) corresponding to Japanese Patent Application No. 2022-095609 dated Dec. 24, 2024. (Translation).

Office Action (Oral proceeding) corresponding to European Patent Application No. 15848390.9 dated Oct. 17, 2024, pp. 8.

Office Action corresponding to European Patent Application No. 15848390.9 dated Jan. 16, 2025, pp. 8.

Office Action received in Chinese Patent Application No. 202411317407.7 mailed on Nov. 28, 2024, 16 pages.

Ramsden, D., et al., "Bridging In Vitro and In Vivo Metabolism and Transport of Faldaprevir in Human Using a Novel Cocultured Human Hepatocyte System, HepatoPac", in Drug Metabolism and Disposition, vol. 42, 2014, pp. 394-406.

Susukida, T., et al., "Prediction of the Clinical Risk of Drug Induced Cholestatic Liver Injury Using an In Vitro Sandwich cultured hepatocyte assay (Drug Metabolism and Disposition)," vol. 43, No. 11, pp. 49 (2015).

Decision of Rejection for Japanese Application No. 2023-061679, dated Mar. 4, 2025, 16 Pages.

Office Action (Notice of Reasons for Rejection) corresponding to Japanese Patent Application No. 2022-095609 dated Apr. 23, 2024 (Translation).

Notice of Reexamination received in Chinese Patent Application No. 201580065533.0 mailed on Oct. 25, 2023, 19 pages (Translation).

* cited by examiner

UTILITY OF PROTEIN IN THE PREDICTION OF IN VIVO EFFECTS

CROSS REFERENCE TO RELATED APPLICATION

This application claims priority to and the benefit of U.S. Provisional Patent Application Ser. No. 62/060,916, filed Oct. 7, 2014, the disclosure of which is incorporated herein by reference in its entirety.

TECHNICAL FIELD

The presently disclosed subject matter relates in some embodiments to a method of evaluating disposition and/or effect of a candidate compound in an in vitro culture and/or suspension to predict in vivo disposition and/or effect of the candidate compound. More particularly, the presently disclosed subject matter relates to a method of evaluating disposition and/or effect, which includes but is not limited to the integrated effects of uptake clearance, basolateral efflux clearance, canalicular efflux clearance, intracellular concentration, biliary clearance, metabolic clearance, and compound kinetics of a candidate compound in an in vitro culture and/or suspension to predict in vivo disposition and/or effect of the candidate compound. In some embodiments, the method involves exposing the culture and/or suspension to a media providing an in vivo relevant extracellular environment, such as a media comprising a component, such a protein, at a physiologic concentration, or at a concentration providing binding characteristics similar to a physiological concentration.

BACKGROUND

Typically, during in vitro experiments using hepatocytes or relevant cell lines (suspended, plated, sandwich-cultured or other 3D models, Caco-2, MDCK, Opti-Target™ (Optivia Biotechnology, Menlo Park, California, United States of America) and those available under the trademark HepaRG® (Biopredic International, Saint Grégoire, France) there are no or non-physiological levels of protein present during the experiments. Therefore, it is only the unbound drug concentration that is being evaluated in all of these experiments. This is often done for reasons of experimental simplicity. In order to translate this into the clinical or in vivo situation, separate in vitro protein binding experiments are performed to determine the fraction of drug bound to plasma proteins, and this information is used to extrapolate any parameters derived from the in vitro experiments to the in vivo situation. That percentage is then, somewhat blindly, applied to results from other experiments by multiplying the percentage to estimate the effect due to "free" compound. The assumption has been that such corrective measures result in a reasonably accurate result that is relevant to a clinical or in vivo situation.

Accordingly, there exists a need for approaches that do not rely on such corrective measures and assumptions. A need exists for method of evaluating the disposition and/or effect of a candidate compound in an in vitro culture and/or suspension to predict in vivo disposition and/or effect of the candidate compound.

SUMMARY

In some embodiments, the method comprises providing a cell culture and/or suspension; exposing a candidate compound to the culture and/or suspension; exposing the culture and/or suspension to a media providing an in vivo relevant extracellular environment, such as a media comprising a component, such as a protein or proteins at physiologic concentrations or a protein concentration demonstrated to have binding characteristics similar to the physiological concentration; and determining an amount of the candidate compound taken up in the culture and/or suspension to thereby evaluate disposition and/or evaluating effect of the compound to predict in vivo disposition and/or effect of the candidate compound.

In some embodiments, provided is a method of evaluating disposition of a candidate compound in an in vitro culture and/or suspension to predict in vivo disposition of the candidate compound. In some embodiments, the method comprises: providing a cell culture and/or suspension; exposing a candidate compound to the culture and/or suspension; exposing the culture and/or suspension to a media providing an in vivo relevant extracellular environment; and determining an amount of the candidate compound taken up in the culture and/or suspension to thereby evaluate disposition of the compound to predict in vivo disposition of the candidate compound. In some embodiments, the cell culture and/or suspension comprises an artificial membrane system adapted to mimic a cell. In some embodiments, the artificial membrane system mimics a cell in co-culture with a supporting cell, wherein the supporting cell comprises a fibroblast cell and/or a kupffer cell. In some embodiments, the cell mimicked by the artificial membrane system is selected from the group consisting of a vesicle, a hepatocyte cell, a liver-derived cell, a renal cell, a gastrointestinal cell, a pancreatic cell, a cardiac cell, a neuronal cell, a myocyte cell, a lipocyte cell, and a pulmonary cell. In some embodiments, the cell mimicked by the artificial membrane system comprises a cell line, optionally wherein the cell line is selected from the group consisting of HepaRG® cell line, Caco-2, and MDC. In some embodiments, determining an amount of the candidate compound taken up in the culture and/or suspension to thereby evaluate disposition comprises: determining an intracellular concentration of the candidate compound; determining hepatic accumulation; determining biliary excretion; and/or determining biliary clearance.

In some embodiments, provided is a method of screening a candidate compound for susceptibility to biliary excretion. In some embodiments, the method comprises: providing a cell culture and/or suspension comprising an artificial membrane system adapted to mimic a cell, and at least one bile canaliculus; exposing a candidate compound to the cell culture and/or suspension; exposing the cell culture and/or suspension to a media providing an in vivo relevant extracellular environment; and determining an amount of the candidate compound in the at least one bile canaliculus to thereby screen the candidate compound for susceptibility to biliary excretion. In some embodiments, determining the amount of the candidate compound in the at least one bile canaliculus comprises: simultaneously exposing to the cell culture and/or suspension for a time sufficient to allow uptake, the candidate compound and a pre-selected amount of a labeled substrate for the transport protein; washing the cell culture and/or suspension; and detecting an amount of the labeled substrate present in the at least one bile canaliculus to evaluate competition between the candidate compound and the labeled substrate for biliary excretion by the transport protein, wherein the presence of a reduced amount of the labeled substrate in the at least one bile canaliculus as compared to the pre-selected amount of the labeled substrate indicates the susceptibility of the candidate compound to biliary excretion by the transport protein. In some embodiments, the artificial membrane system mimics a cell in co-culture with a supporting cell, wherein the supporting cell comprises a fibroblast cell and/or a kupffer cell. In some embodiments, the cell mimicked by the artificial membrane system is selected from the group consisting of a vesicle, a hepatocyte cell, a liver-derived cell, a renal cell, a gastrointestinal cell, a pancreatic cell, a cardiac cell, a neuronal cell, a myocyte cell, a lipocyte cell, and a pulmonary cell. In some embodiments, the cell mimicked by the artificial membrane system comprises a cell line, optionally wherein the cell line is selected from the group consisting of HepaRG® cell line, Caco-2, Opti-Target™ cell line, and MDC. In some embodiments, the labeled substrate comprises a compound selected from the group consisting of a fluorogenic compound, a fluorescent compound, a chemiluminescent compound, a colorimetric compound, a radiolabeled compound and combinations thereof. In some embodiments, the amount of the candidate compound in the at least one bile canaliculus is determined by calculating a biliary clearance value for the culture and/or suspension.

In some embodiments, provided is a method of screening a candidate compound for susceptibility to biliary excretion. In some embodiments, the method comprises: establishing first and second cell cultures and/or suspensions, each first and second culture and/or suspension comprising an artificial membrane system adapted to mimic cells, and at least one bile canaliculus, the first culture and/or suspension having an intact bile canaliculus and the second culture and/or suspension having a disrupted bile canaliculus; exposing a candidate compound to the first culture and/or suspension and to the second culture and/or suspension for a time sufficient to allow uptake of the candidate compound; exposing the first and second cultures and/or suspensions to a media providing an in vivo relevant extracellular environment; washing and lysing the first and second cultures and/or suspensions; and determining an amount of the candidate compound present in a lysate obtained from each culture and/or suspension in step (d) and using the amount of the candidate compound in each culture and/or suspension lysate to evaluate the candidate compound for susceptibility to biliary excretion. In some embodiments, the method comprises: exposing a candidate compound to each of the first and second cultures and/or suspensions for a time (T) sufficient to allow uptake of the candidate compound; exposing the first and second cultures and/or suspensions to a media providing an in vivo relevant extracellular environment; washing and lysing the first and second fractions of each of the first and second cultures and/or suspensions; measuring an amount of candidate compound present in a lysate obtained from each of the first and second cultures and/or suspensions in step (iii); calculating a mass in the bile canaliculi as the difference in the amount of candidate compound present in the lysates from the first culture and/or suspension having intact bile canaliculi and the second culture and/or suspension having disrupted bile canaliculi; and evaluating the candidate compound for susceptibility to biliary excretion using the mass calculated in step (iv). In some embodiments, the artificial membrane system mimics a cell in co-culture with a supporting cell, wherein the supporting cell comprises a fibroblast cell and/or a kupffer cell. In some embodiments, the cell mimicked by the artificial membrane system is selected from the group consisting of a vesicle, a hepatocyte cell, a liver-derived cell, a renal cell, a gastrointestinal cell, a pancreatic cell, a cardiac cell, a neuronal cell, a myocyte cell, a lipocyte cell, and a pulmonary cell. In some embodiments, the cell mimicked by the artificial membrane system comprises a cell line, optionally wherein the cell line is selected from the group consisting of HepaRG® cell line, Caco-2, and MDC.

In some embodiments, provided is a method of evaluating an effect of a candidate compound in an in vitro culture and/or suspension to predict an in vivo effect of the candidate compound. In some embodiments, the method comprises: providing a cell culture and/or suspension; exposing the cell culture and/or suspension to at least one candidate compound at least once; exposing the cell culture and/or suspension to a media providing an in vivo relevant extracellular environment; and evaluating an effect of the exposure of the at least one candidate compound on the cell culture and/or suspension to predict an in vivo effect of the candidate compound. In some embodiments, the method comprises providing a cell culture and/or suspension comprising an artificial membrane system adapted to mimic cells, and at least one bile canaliculus. In some embodiments, the artificial membrane system mimics a cell in co-culture with a supporting cell, wherein the supporting cell comprises a fibroblast cell and/or a kupffer cell. In some embodiments, the cell mimicked by the artificial membrane system is selected from the group consisting of a vesicle, a hepatocyte cell, a liver-derived cell, a renal cell, a gastrointestinal cell, a pancreatic cell, a cardiac cell, a neuronal cell, a myocyte cell, a lipocyte cell, and a pulmonary cell. In some embodiments, the cell mimicked by the artificial membrane system comprises a cell line, optionally wherein the cell line is selected from the group consisting of HepaRG® cell line, Caco-2, Opti-Target™ cell line, and MDC. In some embodiments, the effect is selected from the group consisting of conduction and other types of studies (metabolic, induction and toxicity); metabolism studies including metabolite ID and metabolic stability (parent lifetime); gene regulation (induction/suppression); P450 and transporter drug interactions; subcellular accumulation and free or total (bound+free) intracellular concentration (e.g. nucleus, mitochondria); and a toxicological effect. In some embodiments, the culture and/or suspension is exposed to a plurality of candidate compounds. In some embodiments, the culture and/or suspension is repeatedly exposed to one or more candidate compounds.

In some embodiments of the presently disclosed subject matter, the cells are isolated from a source selected from the group consisting of mouse, rat, rabbit, human, monkey, ape, cat, dog, pig, hog, cattle, oxen, sheep, horses, turkeys, chickens, fish, ducks and geese. In some embodiments of the presently disclosed subject matter, the culture and/or suspension further comprises a long-term culture and/or suspension. In some embodiments of the presently disclosed subject matter, the culture and/or suspension comprises a canalicular network. In some embodiments of the presently disclosed subject matter, the culture and/or suspension is characterized as having a configuration selected from the group consisting of clusters, aggregates, at least one layer of cells, and combinations thereof. In some embodiments of the presently disclosed subject matter, the cells are embedded in a matrix. In some embodiments of the presently disclosed subject matter, the culture and/or suspension further comprises a sandwich culture and/or suspension, the sandwich culture and/or suspension comprising at least one layer of cells and optionally at least one bile canaliculus within the at least one layer of cells. In some embodiments of the presently disclosed subject matter, the sandwich culture and/or suspension further comprises a long-term sandwich culture and/or suspension. In some embodiments of the presently disclosed subject matter, the at least one layer of cells is sandwiched between two layers of matrix. In some
embodiments of the presently disclosed subject matter, the
matrix is selected from the group consisting of a biological
matrix medium, a synthetic matrix medium, co-culture with
supporting cell types, and combinations thereof. In some
embodiments of the presently disclosed subject matter, the
biological matrix medium is selected from the group con-
sisting of collagens, laminins, basement membrane-derived
complexes, derivatives thereof and combinations thereof.

In some embodiments of the presently disclosed subject
matter, the media providing an in vivo relevant extracellular
environment comprises a media comprising a component at
a physiologic concentration or a concentration having a
characteristic similar to a physiological concentration. In
some embodiments of the presently disclosed subject matter,
the component is selected from the group comprising an
albumin, β-lipoprotein, alpha-1-acid glycoprotein, plasma
or serum derived from mouse, rat, rabbit, human, monkey,
ape, cat, dog, pig, hog, cattle, oxen, sheep, horses, turkeys,
chickens, fish, ducks or geese, a bile acid or mixture of bile
acids, bilirubin, and combinations thereof.

In some embodiments of the presently disclosed subject
matter, the method is carried out in at least one well of a
multi-well plate. In some embodiments of the presently
disclosed subject matter, the method further comprises
screening a plurality of candidate compounds simultane-
ously. In some embodiments of the presently disclosed
subject matter, the media comprising a protein at a physi-
ologic concentration comprises another compound that
modulates properties of the candidate compound. In some
embodiments of the presently disclosed subject matter, any
combination of any of the exposing steps can occur in any
order or simultaneously.

It is an object of the presently disclosed subject matter to
provide a method of evaluating disposition and/or effect of
a candidate compound in an in vitro culture and/or suspen-
sion to predict in vivo disposition and/or effect of the
candidate compound.

An object of the presently disclosed subject matter having
been stated hereinabove, and which is achieved in whole or
in part by the presently disclosed subject matter, other
objects will become evident as the description proceeds
when taken in connection with the accompanying examples
as best described herein below.

DETAILED DESCRIPTION

The subject matter disclosed herein will be described
more fully hereinafter, in which some, but not all embodi-
ments of the presently disclosed subject matter are
described. Indeed, the presently disclosed subject matter can
be embodied in many different forms and should not be
construed as limited to the embodiments set forth herein;
rather, these embodiments are provided so that this disclo-
sure will satisfy applicable legal requirements.

In accordance with some embodiments of the presently
disclosed subject matter, provided is a methodology of
adding physiologic or other relevant levels of a component,
such as protein (often referred to generally as albumins),
outside of cells in order to approximate an in vivo environ-
ment since plasma proteins and/or other components are
commonly involved in binding drugs, chemicals, and endog-
enous compounds. Particularly, a more in vivo relevant
extracellular environment will dictate more in vivo relevant
intracellular concentrations and compound kinetics (changes
over time). Both the intracellular concentrations and kinetics
are driving factors in assessing changes in cellular processes and testing cellular outcomes. These processes include
uptake of a compound, efflux (basolateral and canalicular, in
the case of the liver) of the compound, intracellular concen-
tration of the compound, metabolism of a compound, induc-
tion potential of the compound, and toxicity of the com-
pound. Experimental results that were obtained with this
approach were surprising and produced results that would
not be predicted using current methods in the art.

Typically, during in vitro experiments using hepatocytes
or relevant cell lines (suspended, plated, sandwich-cultured
or other 3D models, Caco-2, MDCK, Opti-Target™ (Optivia
Biotechnology, Menlo Park, California, United States of
America), Hμrelflux™ (Hμrel Corporation, North Bruns-
wick, New Jersey, United States of America) and those
available under the trademark HepaRG® (Biopredic Inter-
national, Saint Grégoire, France) there are no or non-
physiological levels of a component such as protein present
during the experiments. Therefore, it is only the unbound
drug concentration that is being evaluated in all of these
experiments. In order to translate this into the clinical or in
vivo situation, separate experiments, such as in vitro protein
binding experiments, are performed to determine for
example the fraction of drug bound to plasma proteins, and
this information is used to extrapolate any parameters
derived from the in vitro experiments to the in vivo situation.
By way of additional example, a protein binding experiment
(such as using equilibrium dialysis) will provide a percent-
age of "free fraction" or fraction unbound (Fu) compound.
That percentage is then, somewhat blindly, applied to results
from other experiments by multiplying the percentage to
estimate the effect due to "free" compound.

Typically, experiments to evaluate the hepatic uptake and
biliary excretion of test compounds are evaluated under
conditions where there is no protein present outside of the
cells. This is often done for reasons of experimental sim-
plicity and typically, the free fraction determined separately
is applied to these results.

In accordance with the presently disclosed subject matter,
it is recognized that blindly applying a free fraction correc-
tion factor to hepatocellular measurements (such as uptake,
biliary excretion, hepatobiliary clearance, or intracellular
concentration) does not provide physiologic data insofar.
Indeed, in a particular example, it is observed that the
addition of protein can change, often drastically, the phar-
macokinetics of uptake of a compound into the cell, alter the
kinetics of uptake proteins, and change the thermodynamic
binding parameters. None of these parameters are consid-
ered, or can be considered, when separately determining the
free fraction. Ultimately, it is the assumption that uptake is
proportional to the unbound drug concentration, which can
be false in many cases. In fact, it is demonstrated herein that
the addition of protein does not always have the anticipated
effect, i.e. the observed uptake and intracellular concentra-
tion of compound does not match the predicted uptake in the
presence of protein. This observation is unexpected.

Indeed, as demonstrated and discussed in the Examples
section herein, experimental data surprisingly demonstrate
that for some compounds, the in vivo biliary clearance and
hepatic intracellular concentration in the presence of condi-
tions that approximate an in vivo environment, such as the
presence of protein, cannot be predicted by adjusting data
with free fraction values obtained from separate studies
(two-step methodology). Rather, performing the evaluations
in the presence of conditions that approximate an in vivo
environment, such as but not limited to physiologic concen-
trations of protein, provided for the determination of an in
vivo relevant value for these parameters. Thus, as demonstrated herein, estimated or calculated (as opposed to observed) biliary clearance and hepatic intracellular concentration can in some instances be surprisingly and dramatically over- or under-predicted.

Accordingly, provided herein in some embodiments is an approach employing an integrated system that combines an in vivo relevant extracellular environment (e.g. protein and/or other component binding effects) with intracellular disposition and/or effect evaluation, such as hepatocellular disposition and/or toxicity.

In some embodiments, the presently disclosed subject matter comprises exposing a candidate compound to a culture and/or suspension; and exposing the culture and/or suspension to a media providing an in vivo relevant extracellular environment, such as a media comprising a component (such as a protein and/or other component) at a physiologic concentration or a concentration having characteristics, such as binding characteristics, similar to the physiological concentration. Some embodiments of the presently disclosed subject matter comprise simultaneous exposure of the candidate compound and the component in the uptake media. Indeed, the presently disclosed subject includes any combination of exposure steps in any order or simultaneously. In some embodiments the media comprises a protein and contains another component that can modulate properties of the candidate compound. Thus, in some embodiments, one can expose the culture and/or suspension to a putative inducer or inhibitor in the presence of media containing protein and then perform an evaluation with media that contains the candidate compound but does not contain protein. Further, in some embodiments, the protein can be a mixture of proteins (albumin, alpha-1-acid glycoprotein at physiological concentrations or at concentrations determined to have similar binding characteristics to those observed at physiological protein concentrations. Also included would be serum or plasma directly obtained from a species of interest.

In some embodiments of the presently disclosed subject matter, hepatocyte cultures, such as sandwich-cultured hepatocytes, can be used to evaluate the hepatic uptake and biliary excretion of compounds of interest, such as drug compounds. As disclosed in U.S. Pat. No. 6,780,580, incorporated herein by reference in its entirety, the screening of compounds of interest, e.g. therapeutic compositions, is desirable as such compounds can be taken up and excreted extensively through the biliary excretion processes whereby they have a minimal chance of imparting therapeutic effects in a subject. It is thus desirable to establish an in vitro test for a compound's susceptibility to hepatocyte uptake and biliary excretion so as to facilitate elimination of a compound with an undesirably high susceptibility from further evaluation as a therapeutic agent early in the evaluation process. Accordingly, because cultures of hepatocytes maintain desired functional properties reflective of in vivo hepatocytes they provide a model for the screening of compounds of interest for susceptibility to biliary excretion. The following U.S. patent documents are also incorporated herein by reference in their entireties: U.S. Pat. Nos. 7,601, 494; 7,682,781; 7,604,934; 8,367,630; and Published U.S. Patent Application No. US-2010-0035293-A1.

As would be appreciated by one of ordinary skill in the art, to accurately model in vivo biological processes at a desirable level, an in vitro culture and/or suspension of cells (such as but not limited to hepatocytes) should be structurally and functionally similar to in vivo cells (such as but not limited to hepatocytes). Thus, in some embodiments of the presently disclosed cultures and/or suspensions, structural and functional properties displayed in vivo are established. For example, the establishment of transport systems, such as sinusoidal or canalicular transport systems, or both sinusoidal and canalicular transport systems is provided in accordance with the presently disclosed subject matter. Particularly, the establishment of at least one bile canaliculus in a cell (such as but not limited to hepatocyte) culture and/or suspension is provided in accordance with the presently disclosed subject matter. A culture and/or suspension can comprise a plurality of bile canaliculi. The plurality of bile canaliculi can comprise a canalicular network. The establishment of at least one bile canaliculus, or canalicular network, can allow for cultured cells (such as but not limited to hepatocytes) to excrete bile and biliary constituents into the at least one bile canaliculus, similar to biliary excretion in vivo.

In addition to the canalicular transport system, establishment of specific transporters in an in vitro hepatic or hepatic-relevant culture is provided. Hepatic-relevant may include completely artificial membrane systems meant to mimic cells, such as vesicles, or cell lines, such as HepaRG® cell line, Hµrelflux™ cell line, Opti-Target™ cell line, Caco-2, and MDCK, that have either been transfected or knocked-out for human-specific proteins (e.g. transporters, P450s). Exemplary transporters include, but are not limited to, Ntcp, cMoat, Oatp1, Oatp2, Mrp2, Mrp3, Pgp, Bsep and Mdr2. The expression and function of these hepatic transporters can be substantially similar to that seen in in vivo hepatocytes.

The establishment of normal metabolic capacity, including metabolic enzyme expression and activity, in the cell (such as but not limited to hepatocyte) culture and/or suspension is also provided in accordance with the presently disclosed subject matter. Thus, the culture can comprise a metabolic capacity that is substantially reflective of in vivo cell (such as but not limited to hepatocyte) metabolism. For example, but not limited to, the normal expression, function and activity of Phase I metabolic enzymes, such as various P450 isozymes, Phase II metabolic enzymes, such as UDP-glucuronosyltransferases (UGT), and other enzymes responsible for the conjugation of primary bile acids to taurine and glycine in an in vitro cell (such as but not limited to hepatocyte) culture and/or suspension are provided in the presently disclosed subject matter.

Thus, in some embodiments, provided herein are methods of evaluating the disposition of a candidate compound in an in vitro culture and/or suspension to predict in vivo disposition of the candidate compound. Such methods can in some embodiments comprise providing a cell culture and/or suspension; exposing a candidate compound to the culture and/or suspension; exposing the culture and/or suspension to a media providing an in vivo relevant extracellular environment, such as a media comprising a component (such as a protein and/or other component) at a physiologic concentration or a concentration having characteristics, such as binding characteristics, similar to the physiological concentration; and determining an amount of the candidate compound taken up in the culture and/or suspension to thereby evaluate disposition of the compound to predict in vivo disposition of the candidate compound. Determining the amount of the candidate compound taken up in the culture and/or suspension to thereby evaluate disposition can further comprises determining an intracellular concentration of the candidate compound, determining hepatic accumulation, determining biliary excretion, and/or determining biliary clearance.

In some embodiments a method of screening a candidate compound for susceptibility to biliary excretion is provided. Such a method of screening a candidate compound for susceptibility to biliary excretion can comprise providing a cell culture and/or suspension (such as but not limited to a suspension comprising an artificial membrane system adapted to mimic a cell), and at least one bile canaliculus; exposing a candidate compound to the cell culture and/or suspension; exposing the cell culture and/or suspension to a media providing an in vivo relevant extracellular environment, such as a media comprising a component (such as a protein and/or other component) at a physiologic concentration or a concentration having characteristics, such as binding characteristics, similar to the physiological concentration; and determining an amount of the candidate compound in the at least one bile canaliculus to thereby screen the candidate compound for susceptibility to biliary excretion.

In some embodiments, the step of determining the amount of the candidate compound in the at least one bile canaliculus can comprise simultaneously exposing to the cell culture and/or suspension for a time sufficient to allow uptake, the candidate compound and a pre-selected amount of a labeled substrate for the transport protein, washing the cell culture and/or suspension, and detecting an amount of the labeled substrate present in the at least one bile canaliculus to evaluate competition between the candidate compound and the labeled substrate for biliary excretion by the transport protein. In some embodiments, the presence of a reduced amount of the labeled substrate in the at least one bile canaliculus as compared to the pre-selected amount of the labeled substrate indicates the susceptibility of the candidate compound to biliary excretion by the transport protein. In some embodiments the amount of the candidate compound in the at least one bile canaliculus is determined by calculating a biliary clearance value for the culture and/or suspension.

Additionally, in some aspects the cell culture and/or suspension in the above methods can comprise an artificial membrane system adapted to mimic a cell, either alone or in co-culture with a supporting cell, such as for example a fibroblast cell and/or a kupffer cell. The cell mimicked by the artificial membrane system can for example include a vesicle, a hepatocyte cell, a liver-derived cell, a renal cell, a gastrointestinal cell, a pancreatic cell, a cardiac cell, a neuronal cell, a myocyte cell, a lipocyte cell, and/or a pulmonary cell. Moreover, in some aspects the cell mimicked by the artificial membrane system can comprise a cell line. In some embodiments, the cell line is selected from the group comprising HepaRG® cell line, Hμrelflux™ cell line, Opti-Target™ cell line, Caco-2, and/or MDC.

Where a labeled substrate is used in any of the methods described herein, such labeled substrate can comprise a compound selected from the group consisting of a fluorogenic compound, a fluorescent compound, a chemiluminescent compound, a colorimetric compound, a radiolabeled compound and/or combinations thereof.

In some embodiments, further methods of screening a candidate compound for susceptibility to biliary excretion are provided. Such methods can comprise establishing first and second cell cultures and/or suspensions and at least one bile canaliculus, the first culture and/or suspension having an intact bile canaliculus and the second culture and/or suspension having a disrupted bile canaliculus. Such methods can further comprise exposing a candidate compound to the first culture and/or suspension and to the second culture and/or suspension for a time sufficient to allow uptake of the candidate compound; exposing the first and second cultures and/or suspensions to a media providing an in vivo relevant extracellular environment, such as a media comprising a component (such as a protein and/or other component) at a physiologic concentration or a concentration having characteristics, such as binding characteristics, similar to the physiological concentration; washing and lysing the first and second cultures and/or suspensions; and determining an amount of the candidate compound present in a lysate obtained from each culture and/or suspension and using the amount of the candidate compound in each culture and/or suspension lysate to evaluate the candidate compound for susceptibility to biliary excretion.

In some embodiments, each first and second culture and/or suspension can comprise an artificial membrane system adapted to mimic cells. Additionally, in some aspects the cell culture and/or suspension in the above methods can comprise an artificial membrane system adapted to mimic a cell, either alone or in co-culture with a supporting cell, such as for example a fibroblast cell and/or a kupffer cell. The cell mimicked by the artificial membrane system can for example include a vesicle, a hepatocyte cell, a liver-derived cell, a renal cell, a gastrointestinal cell, a pancreatic cell, a cardiac cell, a neuronal cell, a myocyte cell, a lipocyte cell, and/or a pulmonary cell. Moreover, in some aspects the cell mimicked by the artificial membrane system can comprise a cell line. In some embodiments, the cell line is selected from the group comprising HepaRG® cell line, Caco-2, and/or MDC.

In some embodiments this method that employs first and second cell cultures and/or suspensions can further comprise exposing a candidate compound to each of the first and second cultures and/or suspensions for a time (T) sufficient to allow uptake of the candidate compound; exposing the first and second cultures and/or suspensions to a media providing an in vivo relevant extracellular environment, such as a media comprising a component (such as a protein and/or other component) at a physiologic concentration or a concentration having characteristics, such as binding characteristics, similar to the physiological concentration; washing and lysing the first and second fractions of each of the first and second cultures and/or suspensions; measuring an amount of candidate compound present in a lysate obtained from each of the first and second cultures and/or suspensions; calculating a mass in the bile canaliculi as the difference in the amount of candidate compound present in the lysates from the first culture and/or suspension having intact bile canaliculi and the second culture and/or suspension having disrupted bile canaliculi; evaluating the candidate compound for susceptibility to biliary excretion using the mass calculated.

In some embodiments methods are provided for evaluating an effect of a candidate compound in an in vitro culture and/or suspension to predict an in vivo effect of the candidate compound. These methods can in some embodiments comprise providing a cell culture and/or suspension; exposing the cell culture and/or suspension to at least one candidate compound at least once; exposing the cell culture and/or suspension to a media providing an in vivo relevant extracellular environment, such as a media comprising a component (such as a protein and/or other component) at a physiologic concentration or a concentration having characteristics, such as binding characteristics, similar to the physiological concentration; and evaluating an effect of the exposure of the at least one candidate compound on the cell culture and/or suspension to predict an in vivo effect of the candidate compound. The effect evaluated in the above methods can in some embodiments comprise conduction and other types of studies (metabolic, induction and toxicity); metabolism studies including metabolite ID and metabolic stability (parent lifetime); gene regulation (induction/suppression); P450 and transporter drug interactions; subcellular accumulation and free or total (bound+free) intracellular concentration (e.g. nucleus, mitochondria); and/or a toxicological effect.

Moreover, in some aspects such a method can further comprise providing a cell culture and/or suspension comprising an artificial membrane system adapted to mimic cells, and at least one bile canaliculus. In some aspects the cell culture and/or suspension in the above methods can comprise an artificial membrane system adapted to mimic a cell, either alone or in co-culture with a supporting cell, such as for example a fibroblast cell and/or a kupffer cell. The cell mimicked by the artificial membrane system can for example include a vesicle, a hepatocyte cell, a liver-derived cell, a renal cell, a gastrointestinal cell, a pancreatic cell, a cardiac cell, a neuronal cell, a myocyte cell, a lipocyte cell, and/or a pulmonary cell. Moreover, in some aspects the cell mimicked by the artificial membrane system can comprise a cell line, such as but not limited to a cell line is selected from the group comprising HepaRG® cell line, Hμrelflux™ cell line, Opti-Target™ cell line, Caco-2, and/or MDC. Such cells can in some embodiments be isolated from a source selected from the group consisting of mouse, rat, rabbit, human, monkey, ape, cat, dog, pig, hog, cattle, oxen, sheep, horses, turkeys, chickens, fish, ducks and geese. In some aspects the culture and/or suspension in the disclosed methods can further comprises a long-term culture and/or suspension. The culture and/or suspension can comprise a canalicular network. The culture and/or suspension can be characterized as having a configuration selected from the group consisting of clusters, aggregates, at least one layer of cells, and combinations thereof. The cells can be embedded in a matrix in some embodiments.

Moreover, in some aspects the culture and/or suspension in the disclosed methods can further comprise a sandwich culture and/or suspension, the sandwich culture and/or suspension comprising at least one layer of cells and optionally at least one bile canaliculus within the at least one layer of cells. The sandwich culture and/or suspension can further comprise a long-term sandwich culture and/or suspension. An at least one layer of cells can be sandwiched between two layers of matrix, wherein the matrix can be selected from the group consisting of a biological matrix medium, a synthetic matrix medium, co-culture with supporting cell types, and combinations thereof. A biological matrix medium can be selected from the group consisting of collagens, laminins, basement membrane-derived complexes, derivatives thereof and combinations thereof.

In any of the methods disclosed herein the culture and/or suspension can in some embodiments be exposed to a plurality of candidate compounds. In some embodiments in the methods disclosed herein the culture and/or suspension can be repeatedly exposed to one or more candidate compounds.

By way of example and not limitation, in the methods disclosed herein the component (such as protein) that can be added at a physiologic concentration or a concentration having characteristics, such as binding characteristics, similar to the physiological concentration can comprise an albumin, alpha-1-acid glycoprotein, β-lipoprotein, bilirubin, a bile acid or a mixture of bile acids, and/or a plasma or serum derived from a representative or desired subject, such as a mouse, rat, rabbit, human, monkey, ape, cat, dog, pig, hog, cattle, oxen, sheep, horse, turkey, chicken, fish, duck or goose. Additionally, in some aspects the media providing an in vivo relevant extracellular environment, such as a media comprising a component (such as a protein and/or other component) at a physiologic concentration or a concentration having characteristics, such as binding characteristics, similar to the physiological concentration can comprise another compound that modulates properties of the candidate compound. Additionally medias comprising a bile acid or a mixture of bile acids, bilirubin, β-lipoprotein, and a protein or protein mixture can comprise another compound that modulates the properties of the candidate compound. Further, concentrations of a component (such as a protein and/or other component) in addition to physiological also include concentrations that might be higher or lower, but have a similar effect. Thus, in some embodiments, non physiological concentrations having a similar effect, such as a similar binding effect, are also provided.

In the methods disclosed herein, such methods can be carried out in at least one well of a multi-well plate. In such methods a plurality of candidate compounds can be screened simultaneously. Moreover, in the disclosed methods, any combination of any of the exposing steps can occur in any order, or simultaneously.

Representative calculations that can be employed in accordance with the presently disclosed subject matter include the calculations of a biliary excretion index and a biliary clearance value. In some embodiments, the biliary excretion index (BEI) indicates the percentage of compound that is taken up into the hepatocyte that is excreted into the bile and the biliary clearance value indicates the potential of the compound to be eliminated into the bile and is the best predictor of elimination of compound into the bile in vivo. In some embodiments, the BEI is a calculation of the uptake and excretion of the candidate compound as follows: 100%× {(uptake in the culture with intact bile canaliculi minus uptake within hepatocytes only in the $Ca^{2+}$-free culture) divided by (uptake in the culture with intact bile canaliculi)}. In some embodiments, the biliary clearance calculation is performed as follows: (uptake in the culture with intact bile canaliculi minus uptake within hepatocytes only in the $Ca^{2+}$-free culture) divided by (time of incubation multiplied by the concentration of the candidate compound in the buffer medium). In some embodiments, a biliary clearance value can be calculated as the ratio of the mass in the bile canaliculi and the area under the curve (AUC) in culture medium, wherein the AUC represents the integral of candidate compound in the medium from time 0 to time T (time can be measure in any desired units, and is usually measured in minutes). Indeed, the term AUC can refer to the following equation:

$$AUC = \int_0^T C\, dT,$$

where C is concentration in medium.
This equation is set forth in the *Pharmacokinetics, Second Edition* (Marcel Dekker, Inc. 1982), by Gibaldi and Perrier, (pp. 13-14).

While the following terms are believed to be well understood by one of ordinary skill in the art, the following definitions are set forth to facilitate explanation of the presently disclosed subject matter.

An "in vivo relevant extracellular environment" is an environment that mimics or approximates an in vivo condition that is relevant for the evaluation of disposition and/or effect of a candidate compound in vitro in accordance with the presently disclosed subject matter. For example, an in vivo relevant extracellular environment can provide a component (such as a protein and/or other component) at a physiologic concentration or a concentration having characteristics, such as binding characteristics, including the extent of binding in addition to the "tightness" (indicated by the $K_a$, association constant or the $K_d$, dissociation constant) of protein binding similar to the physiological concentration.

The combination of terms "disposition and/or effect" includes but is not limited to the following: uptake clearance; basolateral efflux clearance; canalicular efflux clearance; metabolic clearance; intracellular concentration; compound kinetics; a toxicological effect; metabolite ID and metabolic stability (parent lifetime); gene regulation (induction/suppression); P450 and transporter drug interactions; subcellular accumulation and free or total (bound+free) intracellular concentration (e.g. nucleus, mitochondria); and overall biliary clearance. The combination of terms "disposition and/or effect" also includes pharmacokinetics (PK), which can be broadly defined as (1) how the organism or system acts on the compound of interest and (2) all additive clearances in the culture and/or suspension system (uptake, efflux, metabolism). Indeed, the combination of terms "disposition and/or effect" can include any desired evaluation as would be apparent to one of ordinary skill in the art upon a review of the instant disclosure.

The term "calcium-free buffer" is meant to refer to any buffer that is substantially free of calcium. A non-limiting example of a calcium-free buffer is calcium-free Hank's balanced salt solution. As can be appreciated by one of ordinary skill in the art, any suitable buffer that is substantially free of calcium falls within the scope of the presently disclosed subject matter. Employing calcium-free buffer provides for disrupted bile canaliculi in accordance with some embodiments of the presently disclosed subject matter.

The phrases "normal metabolic function(s)", "normal metabolic activity" and "desired metabolic characteristics" are used interchangeably herein and are meant to refer to the activity, function and/or expression of enzymes involved in metabolic pathways and metabolic reactions in a cell, such as but not limited to a hepatocyte cell, under normal basal conditions in vivo.

The term "functional properties" includes any biological property that imparts a specified function involved in the biology of the organism, cell or biochemical reaction. In accordance with the presently disclosed subject matter, functional properties can include enzyme activity, enzyme function, enzyme expression, transporter expression and transporter function, and regulatory pathways responsible for the enzyme and transporter expression.

The terms "compound", "candidate compound", "compound of interest", or "drug compound" are used interchangeably herein and are meant to refer to any compound (exogenously administered or endogenously generated) wherein the characterization of the compound's metabolism, toxicity, hepatic uptake or susceptibility to biliary excretion is desirable. Exemplary compounds, compounds of interest or drug compounds include xenobiotics such as drugs and other therapeutic agents, carcinogens and environmental pollutants and endobiotics such as steroids, bile acids, fatty acids and prostoglandins.

The compounds of interest that are therapeutic agents can be useful in the treatment of warm-blooded vertebrates. Therefore, the presently disclosed subject matter concerns mammals and birds.

Provided is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, provided is the treatment of livestock, including, but not limited to, domesticated swine (pigs and hogs), ruminants, horses, poultry, and the like.

The phrase "evaluating a toxicological effect" is meant to refer to any suitable method of quantitatively and/or qualitatively measuring one or more toxic effects of a compound on a cell, such as but not limited to a hepatocyte.

The term "biliary excretion" is meant to refer to a biological process wherein substances are removed from a subject's circulatory system by being taken up by hepatocytes and excreted in bile via the bile canaliculi, i.e. uptake and efflux. For example, uptake into the hepatocytes is mediated by transport systems endogenous to hepatocytes, including, but not limited to, Ntcp, Oatp1 and Oatp2. Excretion into the bile canaliculi is mediated by efflux transporters, including, but not limited to, Mrp2, Mdr3, Pgp and Bsep. Bile canaliculi are structures within liver tissue which receive excreted components from the hepatocytes and transport the bile to a bile duct for removal from the subject.

The presently disclosed methods can comprise establishing a sandwich-culture of hepatocytes wherein at least one hepatocyte layer is formed between two layers of matrix. While configuration as a sandwich-culture is the preferred configuration for the culture, any suitable configuration as would be apparent to one of ordinary skill in the art is within the scope of the presently disclosed subject matter. For example, clusters, aggregates or other associations or groupings of cells (such as but not limited to hepatocytes) in a culture or suspension wherein at least one bile canaliculus is formed and wherein functional properties of cells (such as but not limited to hepatocytes) are established fall within the scope of the presently disclosed subject matter. In addition, cells (such as but not limited to hepatocytes) in a co-culture with other cell types such as kupffer cells and fibroblasts or other cell types derived from primitive mesenchyme are also within the scope of the presently disclosed subject matter. Optionally, the culture and/or suspension configuration facilitates the formation of a plurality of bile canaliculi reflective of in vivo hepatocytes. Also optionally, the culture configuration facilitates the formation of a canalicular network. Further, the culture configuration optionally facilitates the establishment of a culture of cells (such as but not limited to hepatocytes) with desired metabolic characteristics substantially similar to that of in vivo cells (such as but not limited to hepatocytes). Likewise, desired transporter expression and function are optionally established so as to be substantially similar to that of in vivo cells (such as but not limited to hepatocytes).

Additionally, in a sandwich configuration, cells (such as but not limited to hepatocytes) can be cultured in monolayers between two layers of matrix or scaffolding. But, the cells (such as but not limited to hepatocytes) can also be embedded in the matrix or can extend non-uniformly through the matrix vertically, horizontally, diagonally, or in any combination thereof, such that one-dimensional, two-dimensional and three-dimensional aggregates are formed. Additionally, cultures and/or suspensions can be established in bioreactor systems, microenvironments or three-dimensional scaffolds, such as but not limited to, a three-dimensional flow-through system. See, for example, Griffith and Naughton, (2002) *Science* 295:1009-1014. Cells (such as but not limited to hepatocyte) cultures and/or suspension can thus be formed by mixing cells (such as but not limited to hepatocytes) with an appropriate matrix and inserting the mixture into a suitable culture container, such as a multi-well plate or culture chamber.

While collagen is a representative substrate or scaffolding for the culture and/or suspension of cells (such as but not limited to hepatocytes), any suitable substrate or scaffolding whether natural, synthetic or combinations thereof as would be apparent to one of ordinary skill in the art is within the scope of the presently disclosed subject matter. For example, other biological substrates, including but not limited to laminin and the basement membrane derived biological cell culture substrate sold under the registered trademark MATRIGEL® by Collaborative Biomedical Products, Inc. (Bedford, Massachusetts, United States of America), comprise suitable substrate or scaffolding material. Synthetic matrix materials, substrate materials or scaffolding materials, which are typically made from a variety of materials such as polymers, also fall within the scope of the presently disclosed subject matter. The variation of component materials with a particular matrix for use in culturing cells (such as but not limited to hepatocytes) is also provided in accordance with the methods of the presently disclosed subject matter.

Any suitable source of cells (such as but not limited to hepatocytes) as would be apparent to one of ordinary skill in the art upon review of the present disclosure is within the scope of the presently disclosed subject matter. Exemplary sources include the warm-blooded vertebrates listed above. In particular, exemplary sources include, but are not limited to, human beings, rats, mice, monkeys, apes, cats, dogs, pigs, hogs, cattle, oxen, sheep, horses, turkeys, chickens, ducks and geese.

The cultured cells (such as but not limited to hepatocytes) can be cultured as a "long-term culture and/or suspension". By "long-term culture and/or suspension" it is meant to refer to cells (such as but not limited to hepatocytes) that have been cultured for at least about 12 hours. Optionally, by "long-term culture and/or suspension" it is meant to refer to cells (such as but not limited to hepatocytes) that have been cultured for at least about 24 hours, for at least about 48 hours, or for at least about 72 hours. Also optionally, by "long-term culture and/or suspension" it is meant to refer to cells (such as but not limited to hepatocytes) that have been cultured for at least about 96 hours, at least about one week, or at least about 28 days. Long-term culturing facilitates the formation of bile canaliculi and the establishment of functional properties, such as metabolic pathways, within the culture and/or suspension.

While liver cell cultures and/or suspensions are described herein above as representative cultures, the presently disclosed subject matter provides for the culturing and use of any cell of interest or any combination of cell types alone or with supporting cells that may modulate the function of the disclosed cell types. Thus, upon a review of the instant disclosure, one of ordinary skill in the art can adapt the descriptions and approaches presented herein above for use with any desired cell culture and/or suspension. Representative cell cultures and/or suspensions include but are not limited to a cell culture and/or suspension comprising a cell selected from the group comprising a liver cell, a renal cell, a gastrointestinal cell, a pancreatic cell, a muscle cell, a cardiac cell, a neuronal cell, and a pulmonary cell. In accordance with some embodiments of the presently disclosed subject matter provided is the co-culture of single or multiple cell types with other cells that provide supporting matrix (such as but not limited to fibroblasts) or function (such as but not limited to kupffer cells).

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used in the specification, the presently disclosed and claimed subject matter can include the use of either of the other two terms.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p value". Those p values that fall below a user-defined cutoff point are regarded as significant. In some embodiments, a p value less than or equal to 0.05, in some embodiments less than 0.01, in some embodiments less than 0.005, and in some embodiments less than 0.001, are regarded as significant. Accordingly, a p value greater than or equal to 0.05 is considered not significant.

EXAMPLES

The results of several exemplary experiments comparing the hepatobiliary disposition of multiple compounds in the absence and presence of different types of protein are discussed below. The following examples have been included to illustrate representative modes of the presently disclosed subject matter. In light of the present disclosure, one of ordinary skill in the art will appreciate that the following examples are intended to be representative only and that numerous changes, modifications and alterations can be employed without departing from the spirit and scope of the presently disclosed subject matter.

Example 1

Evaluation of Free Fraction Values for Select Compounds

Initially, several compounds were first identified, using equilibrium dialysis methods, which have a range of free fractions (also called fraction unbound). The free fraction is the amount of compound that is considered thermodynamically free in solution compared to the amount which is considered to be thermodynamically bound to the albumin proteins. For example, a free fraction of 0.428 indicates approximately 43% of the compound is unbound and free in solution under these conditions. These values are shown in Table 1.

TABLE 1

Free Fraction Values for Select Compounds

| Compound | Free Fraction in 4% BSA | Free Fraction in Serum |
|---|---|---|
| Methotrexate | 0.428 | 0.499 |
| Valsartan | 0.075 | 0.004 |
| DPDPE (10 uM) | 0.786 | 0.451 |
| Pravastatin | 0.734 | 0.554 |
| DPDPE (1 uM) | 0.786 | 0.451 |
| Digoxin | 0.852 | 0.727 |
| Taurocholate | 0.142 | 0.047 |
| Pitavastatin | 0.047 | 0.004 |
| Rosuvastatin | 0.136 | — |

Example 2

Evaluation of Measured Intrinsic Biliary Clearance in Rat Hepatocytes

Using the compounds listed in Table 1, the hepatic uptake, efflux, intracellular concentration, and biliary clearance of nine compounds were evaluated in the presence and absence of a physiologic concentration of protein (4% Bovine Serum Albumin, BSA) and serum obtained from Wistar rats. The data for each compound was determined in sandwich-cultured rat hepatocytes at a concentration of 1 μM and an exposure time of 10 minutes in buffer (no protein), in buffer with 4% BSA, or in rat serum. Specifically, the parameters determined were: total accumulation (reflective of uptake, determined under +Ca conditions), cellular accumulation (reflective of intracellular concentration determined under −Ca conditions), the biliary excretion index (BEI; indicates the percentage of compound that is taken up into the hepatocyte that is excreted into the bile), and the intrinsic biliary clearance (indicating the potential of the compound to be eliminated into the bile and is the best predictor of elimination of compound into the bile in vivo). The intrinsic biliary clearance results, which take into account both uptake and efflux of a compound, are shown in Table 2. Taken together, these data clearly show that the addition of extracellular proteins can yield very different results as compared to traditional results measured in buffer.

TABLE 2

The Intrinsic Biliary Clearance in Rat Hepatocytes Under Different Extracellular Conditions

| Compound | No Protein | Std. Dev | BSA | Std. Dev | Serum | Std. Dev |
|---|---|---|---|---|---|---|
| Methotrexate | 0.54 | 0.4 | 0.19 | 0.14 | 0.91 | 0.468 |
| Valsartan | 4.73 | 1.11 | 3.06 | 1.57 | 1.39 | 1.3 |
| DPDPE (10 uM) | 5.39 | 1.33 | 4.23 | 1.04 | 4.09 | 1.67 |
| Pravastatin | 7.35 | 1.31 | 6.47 | .85 | 2.06 | |
| DPDPE (1 uM) | 7.24 | 2.38 | 3.19 | 1.79 | 3.09 | 0.86 |
| Digoxin | 10.4 | 2.74 | 9.25 | 1.83 | 5.12 | 1.65 |
| Taurocholate | 32.5 | 16.5 | 40.40 | 14.50 | 27.90 | 17.1 |
| Pitavastatin | 52 | 6.05 | 140 | 48 | 277.50 | |
| Rosuvastatin | 53.1 | 1.73 | 164.00 | 17.70 | | |

Example 3

Comparison of Measured (Observed) and Calculated (Predicted) Intrinsic Biliary Clearance in Rat Hepatocytes As a next step, experiments were performed to compare the biliary clearance of these same compounds in rat hepatocytes in the presence of extracellular protein with the intrinsic biliary clearance, measured in the absence of protein and has then been adjusted using the appropriate free fraction values (Predicted biliary clearance) in Table 1. This latter method is the current industry standard. Table 3 summarize these results and show the effect of utilizing a one-step, integrated system to measure biliary clearance as compared to a two-step process based on separate experiments. If the two-step method was equivalent, then these values would align. However, there are several exceptions, including pitavastatin and rosuvastatin, where the Predicted biliary clearance is under-estimated by a significant amount, likely due to unanticipated changes in uptake when albumin is present. Note also that the Predicted biliary clearance of DPDPE at 1 μM was over-estimated. The observation that the clearance can be either over- or under-estimated in this case, or basically that these values are not equivalent, indicates the unexpected nature of the interaction and the desirability to use an integrated methodology when assessing cellular disposition.

TABLE 3

Comparison of Measured (Observed) and Calculated
(Predicted) Intrinsic Biliary Clearance in Rat Hepatocytes

| Compound | Observed Cl (ml/min/Kg) | | Predicted Cl (ml/min/Kg) | |
|---|---|---|---|---|
| | BSA | Std Dev | HBSS | Std Dev |
| Methotrexate | 0.083 | 0.058 | 0.23 | 0.17 |
| Valsartan | 0.229 | 0.118 | 0.36 | 0.08 |
| DPDPE (10 uM) | 3.32 | 0.817 | 4.24 | 1.05 |
| Pravastatin | 4.75 | 0.0627 | 5.39 | 0.96 |
| DPDPE (1 uM) | 2.51 | 1.41 | 5.69 | 1.87 |
| Digoxin | 7.88 | 1.56 | 8.85 | 2.33 |
| Taurocholate | 5.73 | 2.06 | 4.62 | 2.34 |
| Pitavastatin | 6.57 | 2.25 | 2.44 | 0.28 |
| Rosuvastatin | 22.3 | 2.41 | 7.22 | 0.24 |

Normally, one would expect that there would be no difference in the values for biliary clearance (since this value takes into account the extent of protein binding). As one can observe from Table 2, this is true for many of the compounds evaluated, e.g. methotrexate, valsartan, DPDPE, pravastatin, digoxin and taurocholate. However, for two of the compounds pitavastatin and rosuvastatin, the predicted intrinsic biliary clearance value in the presence of protein is much greater than that observed in the absence of protein. The effects observed with serum are similar, although not identical, suggesting that protein composition can also have an effect on the clearance prediction for a compound.

Example 4

Comparison of Measured (Observed) and Calculated (Predicted) Intracellular Concentration in Rat Hepatocytes The hepatic intracellular concentration (ICC) of a compound, which reflects the balance of the uptake, metabolism, and efflux out of the cell, can also be determined in the absence and presence of protein. In a similar manner as in Example 3 above, a comparison of a one-step methodology using protein within the system can be compared to data from a two-step methodology where the ICC is determined and adjusted using the free fraction values in Table 1. Table 4 provides results comparing the observed intracellular concentrations using the one-step integrated method of various compounds with the predicted values when the experiments are performed first in the absence of protein and then adjusted using the protein binding data from a separate experiment. If these methods were equivalent, then these values should closely match.

TABLE 4

Comparison of Measured (Observed) and Calculated
(Predicted) Intracellular Concentration in Rat Hepatocytes

| Compound | Observed ICC (uM) BSA | Predicted ICC (uM) HBSS |
|---|---|---|
| Methotrexate | 0.47 | 0.48 |
| Valsartan | 0.22 | 0.44 |
| DPDPE (10 uM) | 15.51 | 13.63 |
| Pravastatin | 2.36 | 1.10 |
| DPDPE (1 uM) | 1.98 | 1.42 |
| Digoxin | 1.29 | 1.59 |
| Taurocholate | 0.10 | 0.13 |
| Pitavastatin | 4.15 | 1.29 |
| Rosuvastatin | 6.81 | 3.09 |

For some of the compounds, integration of the protein binding information from a separate experiment with intracellular concentration data obtained in the absence of protein (Predicted ICC) showed agreement with the observed values for intracellular concentration (Observed ICC). However, for four compounds (valsartan, pravastatin, pitavastatin, and rosuvastatin) the intracellular concentration could not be predicted and was either over-(valsartan) or under-predicted (pravastatin, pitavastatin and rosuvastatin) by greater than 50%. Without measurement using an integrated system, it would not be possible to predict how much of a compound was taken up in to a cell and the resulting intracellular concentration.

These data demonstrate that for some compounds, the in vivo biliary clearance and hepatic intracellular concentration in the presence of protein (physiologic conditions) cannot be predicted by adjusting data with free fraction values obtained from separate studies (two-step methodology). It is only by performing the experiments in the presence of physiologic concentrations of protein that the in vivo relevant value for these parameters can be determined. This effect cannot be predicted based on the protein binding of the compound, as valsartan, pitavastatin, and rosuvastatin are all bound to similar extents to BSA. The effect of the addition of protein on the biliary clearance of valsartan could be readily predicted from protein binding data obtained in a separate study. However, the protein effect on the biliary clearance of pitavastatin and rosuvastatin was unexpected and could not be predicted by using protein binding data from a separate experiment. Accurate estimates of the biliary clearance parameters for pitavastatin and rosuvastatin could only be obtained when the experiment was performed in the presence of a physiologic concentration of protein.

Accurate estimates for biliary clearance are valuable when trying to predict the in vivo clearance prior to first time in human studies. More accurate estimates for the true in vivo clearance can lead to better clinical study design and a decreased need for follow on experiments in humans, and reduced clinical development times.

The hepatic intracellular concentration is a driving force for any process that occurs inside the hepatocyte. Changes in the intracellular concentration can impact any type of interaction that occurs inside the hepatocyte. These can include, but are not limited to: transporter based drug interactions; extent of metabolism of the compound; metabolic interactions; induction potential (metabolic or transport) of the compound; and toxicity produced by the compound or its metabolites.

The observed effects of protein on the intracellular concentration, could lead to an over- or under-prediction of a compound's effect, drastically changing the expected clinical outcome. For example, we have observed this in the case of telmisartan where it was believed to have human cholestatic potential based on its transporter inhibition profile; however, data showed that, in the presence of albumin protein, the intracellular concentration in human hepatocytes in the presence of protein was greater than predicted using data predicted from studies performed in the absence of protein and adjusted using the free fraction by 100×. However, the intracellular concentrations never achieved high enough levels to result in hepatotoxic effects. The in vivo data supports these conclusions as telmisartan has no known toxicity associated with its use. Since the effect of protein was unanticipated and not predictable, it is desirable to expose the cell to protein during the experiment.

An additional example included hepatic accumulation experiments in the presence and absence of a physiologic concentration of BSA to understand the differences in the in vivo toxicity of two compounds where in vitro toxicity tests (performed in the absence of protein) and other pharmacological tests indicated that the two closely related compounds should have the same potential for in vivo toxicity. However, when in vivo tests were conducted, the two compounds had markedly different rodent toxicity (hepatic) profiles. The researchers could not explain the differences based on systemic (blood) exposure. The nontoxic compound (AMG-A) had Cmax concentrations and Area Under the Curve (AUC) values that were 6 times higher than the toxic compound (AMG-B). The researchers then measured the intracellular liver concentrations, and were able that the toxic compound (AMG-B) accumulated to a greater extent in the liver, and had intracellular liver concentrations that were about 15 times higher than AMG-A. The difference in intracellular concentration was able to explain the toxicity differences. (Hamadeh et. al., *Chem. Res. Toxicol.*, 2010, 23 (6), pp 1025-1033).

Example 5

Evaluation of Hepatic Uptake and Intracellular Concentration of AMG-A and AMG-B in the Absence/Presence of a Physiologic Concentration of BSA Experiments to determine the hepatic uptake and intracellular concentration of AMG-A and AMG-B were carried out in sandwich-cultured rat hepatocytes in the absence and presence of a physiologic concentration of protein (4% BSA), in accordance with the presently disclosed subject matter. Significant differences in the hepatic accumulation and intracellular concentrations of the two compounds were observed between the absence and presence of a physiologic concentration of protein. In the experiments performed in the absence of a physiologic concentration of protein (Table 5), the intracellular concentration of AMG-A (non toxic) at the 3 and 10 μM doses was higher than the intracellular concentration of the more toxic compound (AMG-B). It was only when the experiments were performed in the presence of a physiologic concentration of protein (4% BSA) that in vivo relevant intracellular concentrations were achieved (Table 6) where the intracellular concentration of the more toxic compound AMG-B was dramatically higher than the intracellular concentration of the non toxic compound (AMG-A). These results demonstrate that for correct prediction of in vivo effects, the presence of a physiologic concentration of protein is required. The differences in the hepatic accumulation and intracellular concentration of the two compounds in the absence and presence of protein could not be predicted from protein binding data, as the binding parameters were identical for the two compounds.

TABLE 5

Concentration and Time Dependent Uptake of AMG-A and
AMG-B Evaluated in the Absence of Protein (4% BSA).

| No BSA | | Intracellular Concentration (uM) | | | |
|---|---|---|---|---|---|
| Dose | Incubation Time | AMG-A | Std Dev | AMG-B | Std Dev |
| 1 μM | 10 | 51.1 | 14.2 | 77.2 | 8.0 |
| 3 μM | | 158 | 24 | 125 | 16 |
| 10 μM | | 506 | 57 | 313 | 39 |
| 1 μM | 20 | 49.1 | 5.5 | 87.2 | 8.8 |

TABLE 5-continued

Concentration and Time Dependent Uptake of AMG-A and
AMG-B Evaluated in the Absence of Protein (4% BSA).

| No BSA | | Intracellular Concentration (uM) | | | |
|---|---|---|---|---|---|
| Dose | Incubation Time | AMG-A | Std Dev | AMG-B | Std Dev |
| 3 μM | | 169 | 18 | 135 | 9 |
| 10 μM | | 564 | 59 | 364 | 28 |

TABLE 6

Concentration and Time Dependent Uptake of AMG-A and
AMG-B Evaluated in the Presence of Protein (4% BSA).

| BSA | | Intracellular Concentration (uM) | | | |
|---|---|---|---|---|---|
| Dose | Incubation Time | AMG-A | Std Dev | AMG-B | Std Dev |
| 1 μM | 10 | 15.8 | 0.2 | 23.1 | 0.4 |
| 3 μM | | 37.3 | 1.4 | 53.4 | 2.4 |
| 10 μM | | 110 | 2 | 131 | 9 |
| 1 μM | 20 | 17.2 | 0.3 | 27.3 | 1.5 |
| 3 μM | | 40.0 | 2.0 | 66.4 | 0.8 |
| 10 μM | | 113 | 4 | 211 | 4 |

For hepatic systems, the presently disclosed subject matter provides the ability to use protein in the evaluation of the hepatobiliary disposition and/or effect of compounds to predict in vivo relevant biliary clearance and intracellular concentrations. In addition, the presently disclosed subject matter provides for the use of protein in conduction and other types of studies (metabolic, induction and toxicity) that can yield more in vivo predictive results. Thus, in some embodiments, provided are metabolism studies including metabolite ID and metabolic stability (parent lifetime) (Kilford et al., Drug Metab Dispos, 36(7): 1194-1197, July 2008); gene regulation (induction/suppression) (Jackson et al. Chemico-Biological Interactions, 179, 263-272, 2009); P450 and transporter drug interactions (including herbal-drug interactions); subcellular accumulation (Pfeifer et al. Drug Metab Dispos 41:1949-1956, November 2013) and free or total (bound+free) intracellular concentration (e.g. nucleus, mitochondria). As would be apparent to one of ordinary skill in the art upon a review of the instant disclosure, all of the above can employ achieving an in vivo relevant intracellular concentration that is a controlling factor in metabolism, inhibition, induction, regulation and toxicity.

For non-hepatic systems, (e.g. cell lines such as Caco-2, MDCK as well as organ-specific from: kidney, gastrointestinal, pancreatic, cardiac, neuronal, pulmonary), the presently disclosed subject matter provides for the use of relevant protein levels in order to mimic each physiologic situation and derive a protected methodology for measuring compound intracellular concentrations. Knowledge of transporters and the ability to measure intracellular volumes, coupled with the use of an integrated method, allow for the prediction of intracellular concentrations and compound disposition and/or effect (e.g., exposure, efflux, etc.)

Example 6

Evaluation of the Effects of the Addition of Protein on $IC_{50}$ Determinations of P450 Drug Metabolism Enzymes Sandwich-Cultured Hepatocytes (SCH) were prepared using freshly isolated hepatocytes or cryopreserved hepatocytes. Freshly isolated hepatocytes were plated on 24-well cell culture plates, rinsed and fed with the appropriate species specific Qualyst Transporter Solutions (QTS, Durham, North Carolina, United States of America) propriety culture medium (QualGro™). Cells were maintained in the appropriate species specific medium until consumed in studies.

Cryopreserved hepatocytes were thawed following manufacturer's thawing instructions. Cryopreserved hepatocytes were subsequently suspended in QTS propriety hepatocyte seeding medium (QualGro™ Seeding Medium) at a density of 0.7-0.8 million viable cells/mL onto BioCoat® 24-well cell culture plates. Following plating, cells were allowed to attach for 2-4 hours, rinsed and fed with warm (37° C.) seeding medium. Eighteen to 24 hours later, cells were fed and overlaid with the appropriate species specific QTS propriety culture medium (QualGro™) supplemented with extracellular matrix (ECM), Matrigel® (0.25 mg/mL). Cells were maintained in QualGro™ Hepatocyte Culture Medium until consumed in studies.

Cells were cultured as described above through day 6 of culture. On day 7 of culture, spent culture medium was aspirated and replaced with HBSS incubation solution with or without 4% bovine serum albumin (BSA). Incubation solutions including P450 marker substrates and either Fluconazole or Ketoconazole were added directly to the SCHH for a total incubation volume of 0.5 mL. In situ incubations were performed in cell culture incubators (37° C.; 5% CO$_2$; 100% humidity) shaking at 120 rpm for 20-30 minutes. Following the incubation period, incubation solutions were collected and stored at −80° C. until processed for bioanalysis.

In situ incubations were analyzed for the detection of P450 mediated metabolite formation of hydroxymidazolam from midazolam and hydroxyibuprofen from ibuprofen.

Briefly, a volume of 300 µL of internal standard solution (methanol containing 25 nM triazolam and d3-ibuprofen) and a volume of 100 µL of HBSS or HBSS plus 4% BSA were added to a protein precipitation plate (Millipore MDRPNP4; EDM Millipore, Billerica, Massachusetts, United States of America) stacked on a 96 deep well block. The plate was allowed to shake for 1 to 2 minutes prior to centrifugation for collection of the filtered supernatant. The sample filtrate was evaporated to dryness and the samples were reconstituted in 200 µL sample diluent, 40/60 methanol/10 mM ammonium acetate and mixed for at least 20 min on a plate shaker. The reconstituted samples were transferred to a Millipore 0.45 µm filter plate (Millipore MSHVN45) and filtered into a Costar 3957 plate by centrifugation and sealed with a silicone capmat prior to LC-MS/MS analysis.

The direct inhibition effects of the inhibitors, fluconazole (CYP2C9) and ketoconazole (CYP3A4) on enzyme activities of CYP2C9 (3-hydroxyibuprofen) and CYP3A4 (hydroxymidazolam) in SCHH were evaluated in the presence and absence of 4% BSA. Fluconazole (CYP2C9) and Ketoconazole (CYP3A4) reduced CYP2C9 and CYP3A4 enzyme activity to 24.4-45.1% of control and 32.0-71.1% of control, respectively. Positive control inhibitors of CYP2C9 and CYP3A4 reduced enzyme activities in a dose-dependent manner as expected. Differences in the effect of the addition of protein (4% BSA) in the incubation mixture with fluconazole resulted in a decrease in the estimated IC$_{50}$ for CYP2C9 from 56.2 µM to 27.1 µM (Tables 7 and 8), whereas with ketoconazole the estimated IC$_{50}$ for CYP3A4 increased from 0.0455 µM to 0.117 µM (Tables 9 and 10). This emphasizes the differential effects that protein has on the hepatic uptake and intracellular concentration of various compounds, in this case either the probe inhibitors or the probe substrates midazolam and ibuprofen.

TABLE 7

| CYP2C9 Inhibition Positive Control (No BSA) | | | | | |
|---|---|---|---|---|---|
| Treatment | Conc. (µM) | Mean 30HIBU Formation Velocity[†] | Std Dev. Formation Velocity[†] | CYP3A4/5 Mean % Remaining | CYP3A4 Std Dev, % Remaining Activity | Estimated IC$_{50}$ (µM) |
| Fluconazole | 5.00 | 42.9 | 1.0 | 71.1 | 1.7 | 56.2 |
| Fluconazole | 100 | 19.3 | 5.7 | 32.0 | 9.4 | |

[†](pmol/min * million cells)

TABLE 8

| CYP2C9 Inhibition Positive Control (4% BSA) | | | | | |
|---|---|---|---|---|---|
| Treatment | Conc. (µM) | Mean 30HIBU Formation Velocity[†] | Std Dev Formation Velocity[†] | CYP3A4/5 Mean % Remaining | CYP3A4 Std Dev % Remaining Activity | Estimated IC$_{50}$ (µM) |
| Fluconazole | 5.00 | 1.87 | 0.20 | 60.1 | 6.5 | 27.1 |
| Fluconazole | 100 | 0.525 | 0.025 | 16.8 | 0.80 | |

[†](pmol/min * million cells)

TABLE 9

| | | Mean OHMDZ Formation Velocity[†] | Std Dev. Formation Velocity[†] | CYP3A4/5 Mean % Remaining | CYP3A4 Std Dev % Remaining Activity | Estimated IC$_{50}$ (μM) |
|---|---|---|---|---|---|---|
| Treatment | Conc. (μM) | | | | | |
| | | CYP34A Inhibition Positive Control (No BSA) | | | | |
| Ketoconazole | 0.050 | 9.51 | 0.76 | 45.1 | 3.6 | 0.0455 |
| Ketoconazole | 0.250 | 5.14 | 0.042 | 24.4 | 0.20 | |

[†](pmol/min * million cells)

TABLE 10

| | | Mean OHMDZ Formation Velocity[†] | Std Dev Formation Velocity[†] | CYP3A4/5 Mean % Remaining | CYP3A4 Std Dev % Remaining Activity | Estimated IC$_{50}$ (μM) |
|---|---|---|---|---|---|---|
| Treatment | Conc. (μM) | | | | | |
| | | CYP34A Inhibition Positive Control (4% BSA) | | | | |
| Ketoconazole | 0.0500 | 3.36 | 0.56 | 54.6 | 9.1 | 0.117 |
| Ketoconazole | 0.250 | 2.51 | 0.78 | 40.8 | 13 | |

[†](pmol/min * million cells)

REFERENCES

The references cited in the specification are incorporated herein by reference to the extent that they supplement, explain, provide a background for or teach methodology, techniques and/or compositions employed herein.

Griffith and Naughton, (2002) *Science,* 295:1009-1014

Hamadeh et al., (2010) *Chem. Res. Toxicol.,* 23(6):1025-1033

Jackson et al., (2009) *Chemico-Biological Interactions,* 179: 263-272

Kilford et al., (2008) *Drug Metab. Dispos.,* 36(7):1194-1197

Pfeifer et al., (2013) *Drug Metab. Dispos.,* 41:1949-1956

U.S. Pat. No. 6,780,580

U.S. Pat. No. 7,601,494

U.S. Pat. No. 7,604,934

U.S. Pat. No. 7,682,781

U.S. Pat. No. 8,367,630

U.S. Patent Application Publication No. US-2010-0035293-A1

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of evaluating disposition of a candidate compound in an in vitro culture and/or suspension to predict in vivo disposition of the candidate compound, the method comprising:

(a) providing a cell culture and/or suspension, wherein the cell culture and/or suspension comprises a first sandwich culture of hepatocyte cells and providing a second sandwich culture and/or suspension of hepatocyte cells, each first and second sandwich culture comprising an artificial membrane system and at least one bile canaliculus, wherein the artificial membrane system comprises a cell transfected or knocked-out for transporters so as to be adapted to mimic cells, the first sandwich culture having an intact bile canaliculus and the second sandwich culture having a disrupted bile canaliculus;

(b) exposing a candidate compound to the first sandwich culture and to the second sandwich culture for a time sufficient to allow uptake of the candidate compound;

(c) simultaneously exposing the first and second sandwich cultures and/or suspension and the candidate compound to a medium containing proteins that are present extracellularly in liver at physiological concentrations to approximate the in vivo environment of hepatocytes in the liver, wherein the concentration of the proteins contained in the media is a physiologic concentration or a concentration having a characteristic similar to a physiological concentration;

(d) washing and lysing the first and second cell cultures and/or suspensions; and (e) determining an amount of the candidate compound taken up in the first and second sandwich cultures and/or suspension, comprising determining an intracellular concentration of the candidate compound, to thereby evaluate disposition of the compound to predict in vivo disposition of the candidate compound without adjusting using protein binding data from a separate experiment.

2. The method of claim 1, wherein the artificial membrane system mimics a cell in co-culture with a supporting cell, wherein the supporting cell comprises a fibroblast cell and/or a Kupffer cell.

3. The method of claim 1, wherein the cell mimicked by the artificial membrane system is selected from the group consisting of a vesicle, a hepatocyte cell, a liver-derived cell, a renal cell, a gastrointestinal cell, a pancreatic cell, a cardiac cell, a neuronal cell, a myocyte cell, a lipocyte cell, and a pulmonary cell.

4. The method of claim 1, wherein the cell mimicked by the artificial membrane system comprises a cell line, wherein the cell line is selected from the group consisting of hepatocytes, Caco-2, and MDC.

5. The method of claim 1, wherein the cells are isolated from a source selected from the group consisting of mouse, rat, rabbit, human, monkey, ape, cat, dog, pig, hog, cattle, oxen, sheep, horses, turkeys, chickens, fish, ducks and geese.

6. The method of claim 1, wherein the culture and/or suspension further comprises a long-term culture and/or suspension.

7. The method of claim 1, wherein the first sandwich culture and the second sandwich culture and/or suspension further comprise a long-term sandwich culture and/or suspension.

8. The method of claim 1, wherein the protein component is selected from the group comprising an albumin, β-lipo-protein, alpha-1-acid glycoprotein, plasma or serum derived from mouse, rat, rabbit, human, monkey, ape, cat, dog, pig, hog, cattle, oxen, sheep, horses, turkeys, chickens, fish, ducks or geese, bilirubin, and combinations thereof.

9. The method of claim 1, wherein the method is carried out in at least one well of a multi-well plate.

10. The method of claim 1, further comprising screening a plurality of candidate compounds simultaneously.

11. The method of claim 1, wherein the medium containing proteins that are present extracellularly comprises another compound that modulates properties of the candidate compound.

12. The method of claim 1, wherein any combination of any of the exposing steps can occur in any order or simultaneously.

13. The method of claim 12, wherein the protein component is an albumin or serum derived from mouse, rat, rabbit, human, monkey, ape, cat, dog, pig, hog, cattle, oxen, sheep, horses, turkeys, chickens, fish, ducks or geese.

14. The method of claim 1, wherein determining an amount of the candidate compound taken up in the culture and/or suspension to thereby evaluate disposition comprises:

(a) determining hepatic accumulation;

(b) determining biliary excretion; and/or (c) determining biliary clearance.

15. The method of claim 1, wherein the protein component comprises a mixture of protein components.

16. The method of claim 1, wherein the medium comprises a bile acid or mixture of bile acids.

* * * * *